(12) United States Patent
Remijn et al.

(10) Patent No.: US 11,458,805 B2
(45) Date of Patent: Oct. 4, 2022

(54) VAPOR AND PARTICULATE SENSOR SYSTEM FOR AUTOMOTIVE VEHICLES

(71) Applicant: Gentex Corporation, Zeeland, MI (US)

(72) Inventors: Matthew W. Remijn, Grand Rapids, MI (US); Darin D. Tuttle, Byron Center, MI (US); Kurtis L. Geerlings, Zeeland, MI (US); Douglas W. Later, Sandy, UT (US); Benjamin R. Bunes, Murray, UT (US)

(73) Assignee: GENTEX CORPORATION, Zeeland, MI (US)

( * ) Notice: Subject to any disclaimer, the term of this patent is extended or adjusted under 35 U.S.C. 154(b) by 218 days.

(21) Appl. No.: 16/718,612

(22) Filed: Dec. 18, 2019

(65) Prior Publication Data

US 2020/0198436 A1  Jun. 25, 2020

Related U.S. Application Data

(60) Provisional application No. 62/782,976, filed on Dec. 20, 2018.

(51) Int. Cl.
| | |
|---|---|
| *B60H 1/24* | (2006.01) |
| *B60H 1/26* | (2006.01) |
| *B60H 1/00* | (2006.01) |
| *G01N 33/00* | (2006.01) |
| *B60H 3/06* | (2006.01) |

(52) U.S. Cl.
CPC ......... *B60H 1/008* (2013.01); *B60H 1/00792* (2013.01); *B60H 1/265* (2013.01); *G01N 33/0075* (2013.01); *B60H 2003/0683* (2013.01)

(58) Field of Classification Search
CPC ...................................................... B60H 1/008
USPC .................................. 454/75; 700/276–278
See application file for complete search history.

(56) References Cited

U.S. PATENT DOCUMENTS

| | | |
|---|---|---|
| 8,703,500 B2 | 4/2014 | Zang et al. |
| 9,452,989 B2 | 9/2016 | Zang et al. |
| 9,823,193 B2 | 11/2017 | Zang et al. |
| 2010/0043529 A1 | 2/2010 | Wang et al. |

(Continued)

FOREIGN PATENT DOCUMENTS

| | | |
|---|---|---|
| CN | 107705180 A | 2/2018 |
| DE | 102016215525 A1 | 2/2018 |

(Continued)

*Primary Examiner* — Ko-Wei Lin
(74) *Attorney, Agent, or Firm* — Price Heneveld LLP; Brian James Brewer (57) ABSTRACT

An air quality system for a vehicle includes a chemical detection apparatus including a plurality of nanofiber chemical sensors for sensing a plurality of airborne materials in a compartment of the vehicle. The plurality of nanofiber chemical sensors are configured to adjust a characteristic electrical signal in response to changes in the presence of the plurality of airborne materials. The chemical detection apparatus further includes a processor coupled to the nanofiber chemical sensor, wherein the processor is configured to monitor the characteristic electrical signals from the nanofiber chemical sensors and generate a detection signal in response to a change in the characteristic electrical signals. The processor is in communication with a controller configured to control at least one vehicle system in response to the detection of one or more of the airborne materials.

20 Claims, 4 Drawing Sheets

(56) References Cited

U.S. PATENT DOCUMENTS

| | | |
|---|---|---|
| 2012/0122075 A1 | 5/2012 | Call et al. |
| 2014/0235493 A1* | 8/2014 | Zang ................. G01N 33/0031 506/9 |
| 2016/0361972 A1 | 12/2016 | Blackley |
| 2018/0050575 A1* | 2/2018 | Campbell ......... B60R 21/01536 |
| 2018/0074495 A1 | 3/2018 | Myers et al. |
| 2018/0134112 A1* | 5/2018 | Seiferlein .......... B60H 1/00821 |
| 2018/0224849 A1 | 8/2018 | Gordon et al. |
| 2018/0330475 A1 | 11/2018 | Tokatyan |
| 2019/0095714 A1 | 3/2019 | Wilcox et al. |
| 2019/0234642 A1* | 8/2019 | Fetterman .............. G05B 15/02 |
| 2020/0043030 A1 | 2/2020 | Mangal et al. |

FOREIGN PATENT DOCUMENTS

| | | |
|---|---|---|
| EP | 3336540 A1 | 6/2018 |
| WO | 2018053650 A1 | 3/2018 |

\* cited by examiner

VAPOR AND PARTICULATE SENSOR SYSTEM FOR AUTOMOTIVE VEHICLES

CROSS-REFERENCE TO RELATED APPLICATIONS

This application claims priority under 35 U.S.C. § 119(e) and the benefit of U.S. Provisional Application No. 62/782,976 entitled VAPOR AND PARTICULATE SENSOR SYSTEM FOR AUTOMOTIVE VEHICLES, filed on Dec. 20, 2018, by Geerlings et al., the entire disclosure of which is incorporated herein by reference.

TECHNOLOGICAL FIELD

The present invention generally relates to a vehicle detection system and, more particularly, to light assemblies configured to disinfect a passenger compartment.

BACKGROUND OF THE INVENTION

Passenger compartments in vehicles, especially those in shared vehicles or in the on-demand type, may accumulate contaminants over time resulting from use, local environment, and various sources. Some contaminants may result in odors and/or fumes, which may be unfavorable. Additionally, in some cases, contaminants located in the vehicle could present health risks in the form of bacteria, smoke, and/or noxious fumes. Accordingly, methods or systems to detect and identify or mitigate the accumulation of contaminants in the vehicle may be beneficial.

SUMMARY OF THE DISCLOSURE

According to one aspect of the present disclosure, an air quality system for a vehicle is disclosed. The system comprises a chemical detection apparatus comprising a plurality of nanofiber chemical sensors for sensing a plurality of airborne materials in a compartment of the vehicle. The plurality of nanofiber chemical sensors are configured to adjust a characteristic electrical signal in response to changes in the presence of the plurality of airborne materials. The chemical detection apparatus further comprises a processor coupled to the nanofiber chemical sensor, wherein the processor is configured to monitor the characteristic electrical signals from the nanofiber chemical sensors and generate a detection signal in response to a changes in the characteristic electrical signals. The processor is in communication with a controller configured to control at least one vehicle system in response to the detection of one or more of the airborne materials.

According to another aspect of the present disclosure, a method for controlling an air quality system for a vehicle is disclosed. The method comprises sensing a plurality of airborne materials in a compartment of the vehicle via a plurality of nanofiber chemical sensors. The method further comprises monitoring the characteristic electrical signals from the nanofiber chemical sensors and generating a detection signal in response to a changes in the characteristic electrical signals. The method further comprises communicating the detection signal to at least one vehicle system in response to the detection of one or more of the airborne materials.

According to yet another aspect of the present disclosure, an air quality system for a vehicle is disclosed. The system comprises a chemical detection apparatus comprising a plurality of nanofiber chemical sensors for sensing a plurality of airborne materials in a compartment of the vehicle. The plurality of nanofiber chemical sensors are configured to adjust a characteristic electrical signal in response to changes in the presence of the plurality of airborne materials. A processor is coupled to the nanofiber chemical sensors, wherein the processor is configured to monitor the characteristic electrical signals from the nanofiber chemical sensors and generate a detection signal in response to a changes in the characteristic electrical signals. The processor is in communication with a controller configured to access a user profile comprising information identifying a user-defined material associated with the user profile. The user-defined material corresponds to an allergen of the plurality of airborne materials. In response to the activation of the user profile and the detection of the user-defined material exceeding a user-defined detection level, the controller is configured to activate an alert device configured to communicate the detection of the user-defined material.

These and other aspects, objects, and features of the present disclosure will be understood and appreciated by those skilled in the art upon studying the following specification, claims, and appended drawings. It will also be understood that features of each example disclosed herein may be used in conjunction with, or as a replacement for, features of the other examples.

BRIEF DESCRIPTION OF THE DRAWINGS

The following is a description of the figures and the accompanying drawings. The figures are not necessarily to scale, and certain features and certain views of the figures may be shown exaggerated in scale or in schematic in the interest of clarity.

In the drawings.

DETAILED DESCRIPTION OF THE PREFERRED EMBODIMENTS

Figure 1:
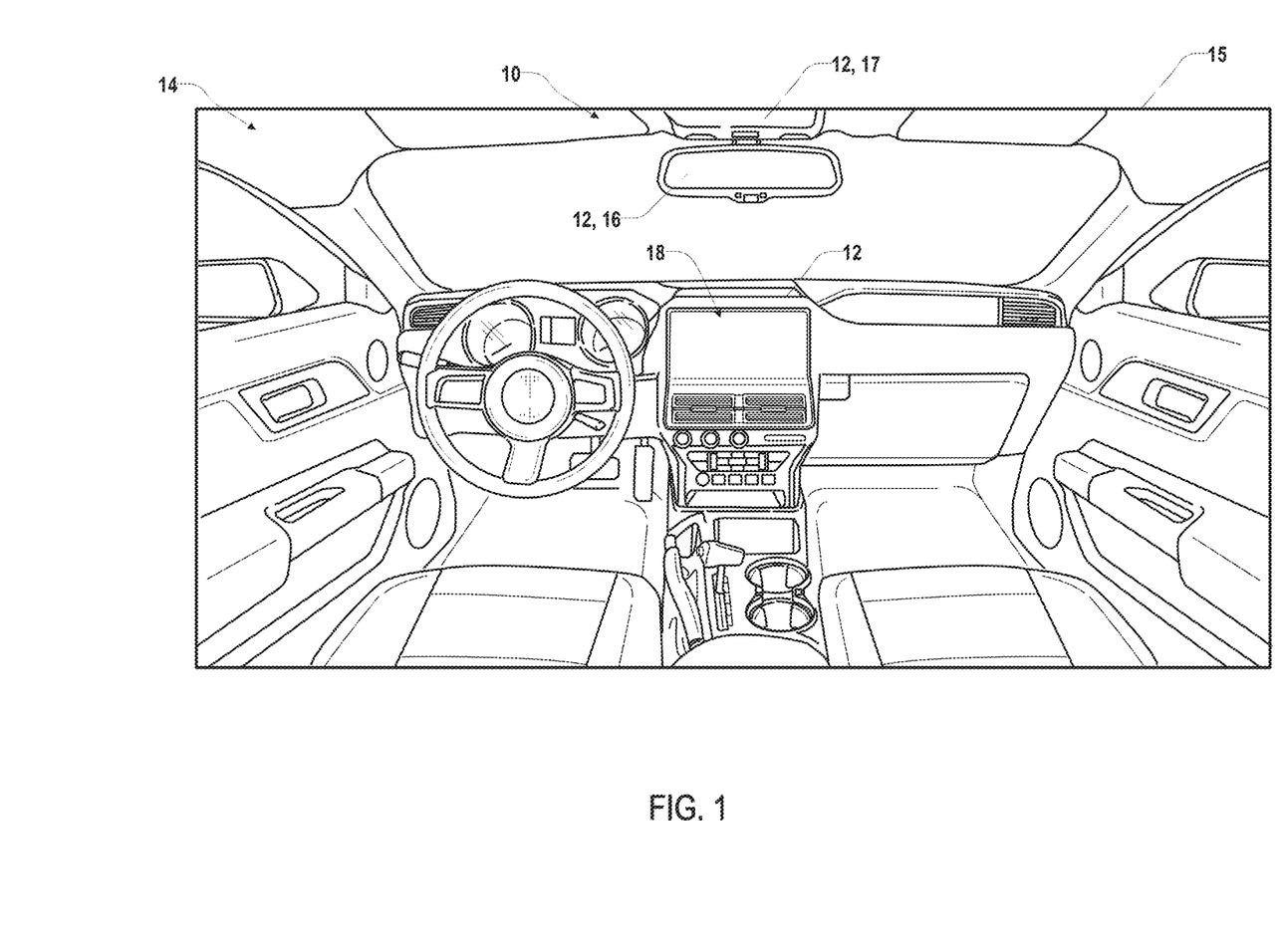
FIG. 1 is a cockpit view of a passenger compartment of a vehicle comprising a chemical detection sensor according to some aspects of the present disclosure.

For purposes of description herein the terms "upper," "lower," "right," "left," "rear," "front," "vertical," "horizontal," and derivatives thereof shall relate to the device as oriented in FIG. 1. However, it is to be understood that the device may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Referring now to FIGS. 1-4, the reference numeral 10 generally designates an air quality detection system. The detection system 10 may comprise a chemical detection device 12, which may be designed to identify a type and/or concentration of various chemicals in a passenger compartment 14 of a vehicle 15. In some examples, the detection device 12 may be incorporated in a rearview mirror or rearview display 16. Though discussed in reference to the rearview display 16, the detection device may be located in various portions of the vehicle 15, some of which are shown in FIG. 1.

The rearview display 16 may be mounted to a vehicle header 17 of the vehicle 15. As shown, the passenger compartment 14 additionally includes the control region 18 including many of the controls a driver or passenger may interact with and touch when using or riding in the vehicle 15. In some aspects, the detection system 10 may be in communication with additional vehicle systems and devices that may be configured to control various ventilation and/or vehicle operating capabilities based on the detection and identification of airborne materials in the passenger compartment 14.

In various embodiments, the chemical detection device 12 may correspond to a variety of sensory devices. For example, the chemical detection device 12 may be implemented by a variety of devices including, but not limited to, electrochemical sensors, amperometric gas sensors, carbon monoxide sensors, catalytic bead sensors, thermal conductivity sensors, metal oxide sensors (MOS), infrared (IR) sensors, photoionization detectors (PID), etc. Such sensors may vary in application and, therefore, may be implemented in various combinations to achieve the identification and detection of various chemicals and contaminants that may be present in the passenger compartment. Though specific examples are discussed herein, the chemical detection device 12 may be implemented by similar sensors or developing sensory technologies without departing from the spirit of the disclosure.

Figure 2:
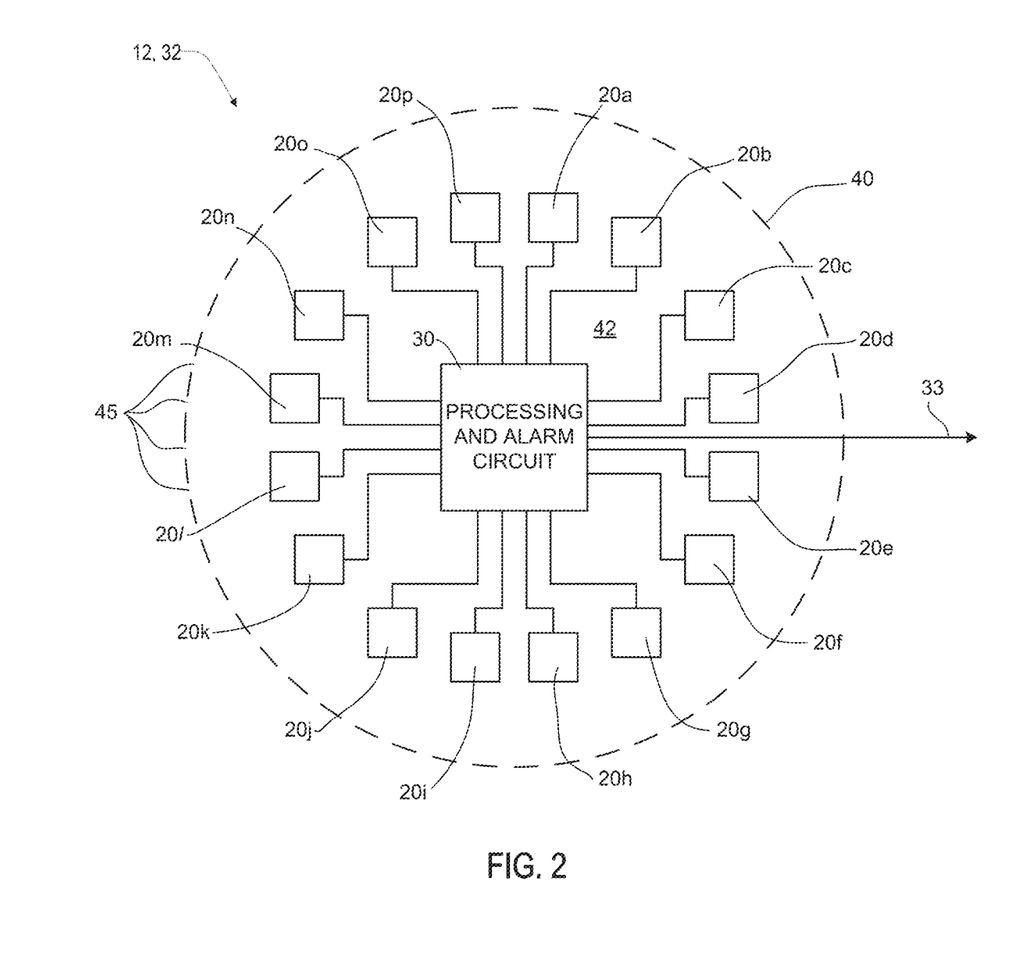
FIG. 2 is an electrical circuit diagram of a chemical detector.

Referring now to FIG. 2, an example of the detection device 12 is shown in communication with at least one nanofiber chemical sensor 20. The nanofiber chemical sensor 20 may be configured to sense various chemicals and compounds that may be present in the ambient air within the passenger compartment 14. In some embodiments, the at least one nanofiber chemical sensor 20 may comprise a plurality of nanofiber chemical sensors 20a-20p. In operation, each of the one or more nanofiber chemical sensors 20 may be in communication with a processor 30, which may be configured to monitor changes in electrical characteristics for each of the nanofiber sensors 20 in the presence of the various airborne materials. Based on the combination of signals received from the at least one nanofiber chemical sensor 20, the processor 30 may be configured to identify the presence of one or more contaminants in the passenger compartment 14.

The nanofibers used in the sensors 20 may be synthesized with specific functional groups that can interact with airborne materials/vapors/particles. The nanofibers are deposited on an interdigitated electrode to form an electrode-nanofiber array. Interaction of the nanofibers with airborne materials changes the measured electrical characteristics of the nanofiber chemical sensor. An increase or decrease in the measured current or effective resistance of each of the nanofiber chemical sensors occurs as a result of these airborne material interactions.

Nanofibers of each of the sensors 20 with different functional groups have a different response to the same airborne material. By using the plurality of nanofiber chemical sensors 20 in an array 32, an identifying response signature can be established by the processor 30 for each of a plurality of airborne materials. Accordingly, based on the electrical signals communicated from the array 32, the processor 30 may be configured to detect a variety of conditions that may exist in the vehicle 15 and/or the passenger compartment 14. The nanofibers of the sensors 20 may have a proportionately large 3-dimensional surface area that is resistant to particulate fouling. In various embodiments, the processor 30 may be configured to identify a variety of contaminants in the passenger compartment 14. In response to the particular contaminant or family of contaminants identified by the detection device 12, the system 10 may be configured to respond by outputting a variety of notifications and/or controlling a variety of vehicle systems.

In various embodiments, the detection device 12 may be configured to identify a variety of chemicals present in the passenger compartment and/or proximate to the vehicle 15. Chemicals and compounds that may be detected by the device 12 may be trained or programmed based on electrical signatures received by the processor 30 in response to the presence of the chemicals. Examples of chemicals that may be identified and/or detected may include, but are not limited to, Benzaldehyde, Hexane, Acetone, Ethanol, Diesel Fuel, Nitrobenzene, and Formaldehyde. Some examples of explosives and chemical agents that may be detected may include Nitromethane, DNT (Dinitrotoluene), TNT (Trinitrotoluene), ANFO (Ammonium Nitrate Fuel Oil), Ammonium Nitrate, PETN (may detect taggant), RDX (may detect taggant), TATP (Triacetone Triperoxide), $H_2O_2$ (Hydrogen Peroxide), TEP (Triethylphosphate), DMMP (Dimethyl methylphosphonate), 2-Chloroethyl ethyl sulfide, Triphosgene, Methyl Salicylate. Some examples of toxic chemicals that may be detected by the detection device 12 may include, but are not limited to, Chlorine Gas, Ammonia, Hydrogen Peroxide, Sulfur Dioxide, Hydrochloric Acid, TEP (Triethyl Phosphate), Phosphine, Hydrogen Cyanide, Arsine, Formaldehyde. In some examples, the detection device may also be configured to detect one or more chemicals commonly found in consumer foods and/or goods including, but not limited to, Trichloroanisole, Melamine, Trimethylamine, Limonene, Pinene, Linalyl acetate, Menthol, Menthone, and Linalool. The device 12 may additionally be configured to detect various amines including, but not limited to, N-Methylphenethylam-lamine, Phenethylamine, Methylamine, Aniline, Triethylamine, and Diethylamine. Accordingly, based on the detection of each of the chemicals detected by the device 12, a controller or control system of the vehicle may provide a corresponding response, which may mitigate an odor, deactivate a vehicle system, output a warning, and/or provide for a variety of beneficial system responses.

Figure 3:
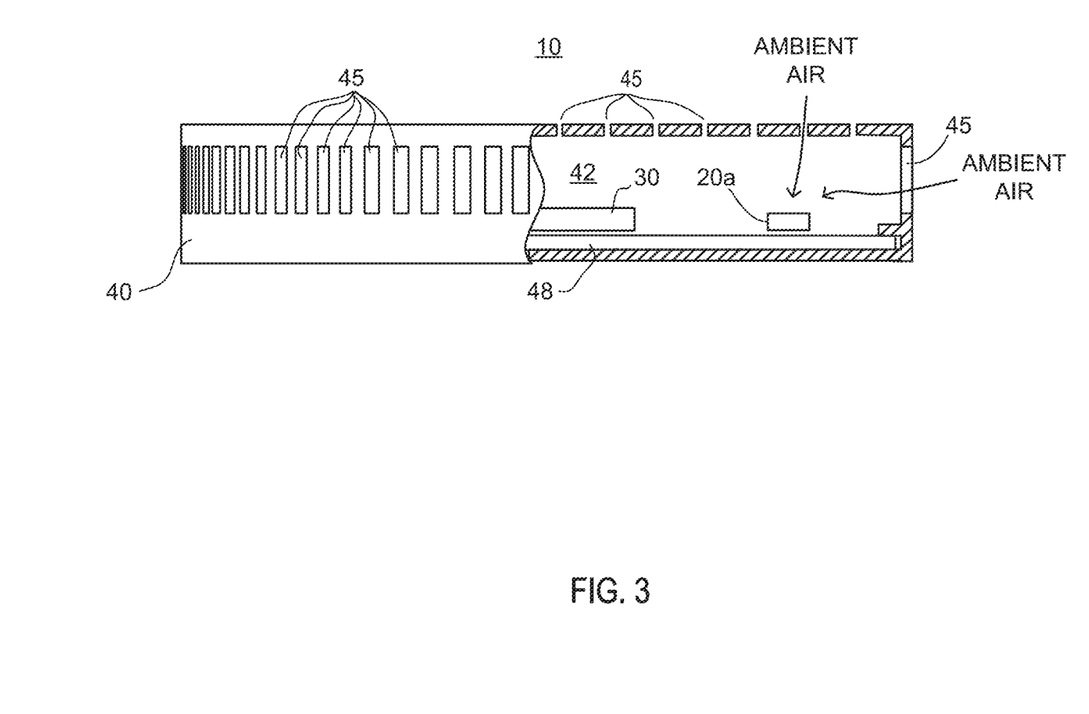
FIG. 3 is a side view of the chemical detection device shown in partial cross-section.

Referring now to FIG. 3, the chemical sensors 20a-20p of the detection device 12 may be arranged in any manner and may be disposed in an inner chamber 42 of a housing 40 having a plurality of air vents 45. The air vents 45 may provide for ambient and/or forced air to flow into the inner chamber 42. In this configuration, updated samples of the air present in the passenger compartment 14 may flow passed the chemical sensors 20a-20p providing consistently updated monitoring of the chemical particulates present in the air. In various implementations, the air vents 45 may be large enough and/or numerous enough to allow the ambient air to flow into inner chamber 42 without restriction. The processor 30 may be in communication with various systems and/or controllers of the vehicle 15 via a connection 33. In various implementations, the connection 33 may correspond to a wired and/or wireless connection. Although the processor 30 and nanofiber chemical sensors 20a-20p are shown in FIG. 3 as being mounted on a common circuit board 48, they may be mounted on separate circuit boards.

Figure 4:
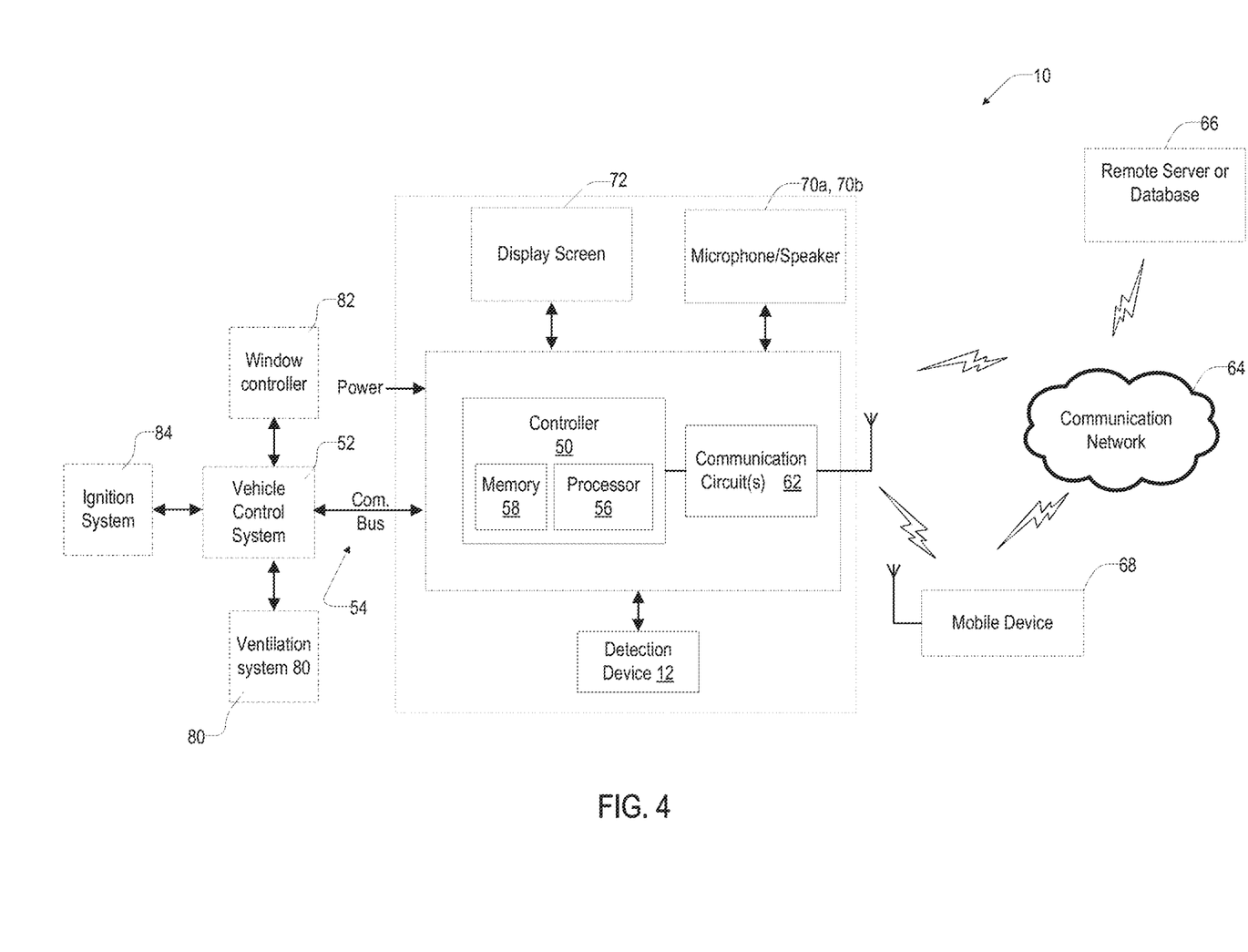
FIG. 4 is a block diagram of a vehicle system comprising a chemical detection sensor in accordance with the disclosure.

Referring to FIG. 4, a block diagram of the system 10 comprising the detection device 12 is shown. The system 10 may comprise a controller 50 incorporating the detection device 12. In FIG. 4, the controller 50 of the system 10 is shown in communication with the detection device 12 via the connection 33. The controller 50 may further be in communication with a control module 52 via a communication bus 54 of the vehicle 15. The communication bus 54 may be configured to deliver signals to the controller 50 identifying various states of the vehicle 15. For example, the controller 50 may be configured to control a variety of vehicle functions via the communication bus 54. For example, the controller may control or communicate an input configured to initiate control of an ignition state, a door or window control status (e.g. open/closed configuration), activation of lighting devices, audible alerts (e.g. horn operation), hazard indications, etc. Such control signals may be submitted from the controller 50 to control various systems of the vehicle 15 via the communication bus 54 or any form of communication (e.g. wired, wireless).

The controller 50 may comprise a processor 56 having one or more circuits configured to control various operations of the system 10. The processor 56 may be in communication with a memory 58 configured to store instructions to control operations of the detection device 12. For example, the controller 50 may be configured to store one or more control responses configured to control various systems of the vehicle in response to the detection of one or more chemicals by the detection device 12.

In some embodiments, the controller 50 may further comprise one or more communication circuits 62 configured to communicate via a communication network 64. Accordingly, the system 10 may be in communication with a remote server 66 and/or a mobile device 68 via the communication network 64. The communication network 64 may comprise one or more wireless or wired network interfaces or communication protocols. As discussed herein, wireless communication protocols may operate in accordance with communication standards including, but not limited to, the Institute of Electrical and Electronic Engineering (IEEE) 802.11 (e.g., WiFi™); Bluetooth®; advanced mobile phone services (AMPS); digital AMPS; global system for mobile communications (GSM); code division multiple access (CDMA); Long Term Evolution (LTE or 4G LTE); local multipoint distribution systems (LMDS); multi-channel-multi-point distribution systems (MMDS); RFID; and/or variations thereof. In this configuration, the controller 50 may be configured to send an alert or message to the mobile device 68 and/or the remote server 66 identifying a detection of a chemical related to the operation of the vehicle 15 and/or a chemical present in the passenger compartment 14. The alert or message may correspond to a text message, data message, email, alert via an application operating on the mobile device 68, etc.

The system 10 may further be in communication with one or more of a microphone 70a and/or a speaker 70b. In such embodiments, the system 10 may be configured to communicate one or more warnings, instructions, and/or additional information to a user in response to the detection of one or more chemicals via the detection device 12. Additionally, the system 10 may be configured to initiate an emergency communication (e.g. a telephonic communication) from the vehicle in response to the detection of a potentially hazardous chemical identified by the detection device 12. In some aspects, the controller 50 may further be in communication with a display screen 72, which may be disposed in various portions of the vehicle for display of images and graphics, which may provide for the control to display instructions and/or warnings related to the detection of one or more chemicals by the detection device 12.

Referring now to FIGS. 1 and 4, various exemplary operations of the system are discussed in reference to the examples provided herein. As generally discussed herein, the system 10 may provide for air quality monitoring within the passenger compartment 14 of the vehicle 15. Contaminants that may be detected in the passenger compartment 14 may be categorized generally as those that relate to passenger comfort related considerations (e.g. odors, perfumes, etc.) and those that relate to potentially dangerous chemicals. In operation, the controller 50 of the system may be configured to control a response of the system 10 to mitigate, control, ignore, and/or counteract the effects of various chemicals that may be detected by the detection device 12. In various examples, the controller 50 may be configured to control the system 10 to respond based on the specific type of chemical, a family of chemicals, and/or general category (hazardous versus non-hazardous) of the chemicals detected by the detection device 12. In this way, the controller 50 may be configured to provide a specific and/or configurable response to resolve the concerns related to the detection of specific chemicals and/or categories of chemicals.

Common chemicals and corresponding odors that may be detected by the device 12 may vary widely. For example, the device 12 may be configured to identify a variety of odors including, but not limited to, perfumes, feces, fish, skunk, pet odor, decaying biological material, methane, hydrogen sulfide, body odor (body-related bacterial odor), smoke, alcohol, bodily fluids, vomit, etc. Some of these odors may relate to comfort issues while others could present health issues to one or more passengers of the vehicle 15. Accordingly, the detection device may additionally communicate a concentration of the chemicals detected in the vehicle to the controller 50. According to the desired configuration, the controller 50 may respond to an indication of the presence of a chemical at a reported level in a variety of ways.

Additionally, the detection device 12 may be configured to detect and identify a variety of chemicals that may generally be considered dangerous which may or may not cause a significant odor. Examples of such chemicals or sources of such chemicals may be allergens including, but not limited to, peanuts, soy, perfumes, smog, etc. Additional examples of chemicals or sources of such chemicals may include, but are not limited to, explosives, gun power, accelerants, carbon dioxide, carbon monoxide, volatile organic compounds (VOCs), drugs (e.g. methamphetamine, alcohol), smog, smoke, exhaust, etc. In response to the detection of such chemicals, the system 10 may respond in different ways, particularly in comparison to the detection of chemicals that may not be dangerous in relation to vehicle operation or passenger health. The nanofiber chemical sensor may be an organic conductive nanofiber chemical sensor. The controller may be configured to identify the detection of the one or more airborne materials in response to one or more of the signals exceeding a predetermined threshold.

As discussed herein, the system 10 may operate in a passive configuration, wherein the controller 50 is configured to report the identification of chemicals via one or more alerts in the vehicle 15 (e.g. via indicators in the control region 18) and/or communications to the remote server 66 and/or a mobile device 68. In such embodiments, the system may communicate the presence of the chemicals to a user or administrator of the vehicle 15 so that proper corrective action may be taken. For example, a notification may be communicated from the controller 50 to the mobile device 68 indicating that there is an odor related to a specific chemical or family of chemicals that should be investigated by a user of the vehicle 15 to limit odor or for maintenance purposes. Accordingly, indications to the remote server 66 and/or a mobile device 68 may be communicated from the controller 50 of the system 10 in response to any chemical detection that may be detected by the detection device 12.

In response to the detection, when a chemical is reported from the detection device 12 to the controller 50, the controller may respond in a variety of ways. For example, in response to the detection of a first chemical, the controller 50 may control a vehicle heating, ventilation, and air conditioning (HVAC) or ventilation system 80 to activate an active filter or air purifier, which may be in connection with an air circulation path or air supply port. Air purifiers that may be utilized may include active UV-C air filters, ionizers, and other types of filters. Additionally, in response to a second chemical, the controller 50 may be configured to activate fresh air ventilation of the ventilation system 80 such that fresh air is drawn into the cabin. In this way, the system 10 may dilute a concentration of the second chemical in passenger compartment 14 to mitigate any discomfort related to the presence of the chemical. In some embodiments, in response to a third chemical, the controller 50 may be configured to control a window controller 82 to open the passenger compartment 14 to ventilate.

Accordingly, the system 10 may provide for a different response in response to detection of each of a plurality of chemicals in the vehicle 15. Though specific chemicals (first, second, third, etc.) are discussed in reference to the corrective actions (e.g. ventilation, filtration, etc.), it shall be understood that the controller 50 may be configured to apply various corrective actions alone or in combination based on a desired configuration of the system 10. For example, in response to the detection of the first chemical, the controller 50 may activate the ventilation system 80 and control the window controller 82 to open one or more windows of the vehicle 15.

In some embodiments, the system 10 may be configured to suppress or deactivate a vehicle ignition 84 in response to a detection of a chemical by the detection device 12. The controller 50 may additionally activate an alarm, alert indicator, or warning, which may be displayed on a screen or indicator of the control region 18 of the vehicle 15. In some embodiments, an instruction may be provided by the alarm or alert, which may instruct the operator or passenger of the vehicle 15 to deactivate or seek maintenance for the vehicle 15. As previously discussed, the control of the vehicle ignition 84, the alarm, and various devices may be configured based on a desired response, which may be tailored to a user, a particular vehicle, geographic region of operation, etc. Accordingly, the system 10 may be configured in a variety of ways to provide control instructions to a variety of vehicle accessories and/or devices.

In some embodiments, the configuration of the system 10 may be configured based on one or more standard warnings, which may relate to the detection of generally dangerous chemicals. Additionally, the system 10 may be configured to provide custom alerts, detections, or corrective actions based on specific allergies, chemicals, and/or odors that a user indicates as being problematic. For example, if an individual has a specific allergy (e.g. peanuts, tree nuts, soy, etc.), the system may be selectively configured to alert at a user-defined detection level in response to the detection of the chemicals related typically identified in relation to the allergen. In this way, the system 10 may provide for customized controls to assign alerts in response to any chemicals that may be detected by the detection device 12.

It will be understood by one having ordinary skill in the art that construction of the described device and other components may not be limited to any specific material. Other exemplary embodiments of the device disclosed herein may be formed from a wide variety of materials unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the device as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structure without departing from the concepts of the present invention, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

What is claimed is:

1. An air quality system fora vehicle comprising:
   a chemical detection apparatus comprising a plurality of nanofiber chemical sensors configured to detect a first chemical and a second chemical different than the first chemical, the first and second chemicals associated with a plurality of airborne materials in a compartment of the vehicle, wherein the plurality of nanofiber chemical sensors are each configured to adjust a characteristic electrical signal in response to changes in the presence of the plurality of airborne materials; and
   a processor coupled to the plurality of nanofiber chemical sensors, wherein the processor is configured to monitor the characteristic electrical signal from each of the plurality of nanofiber chemical sensors, generate a detection signal in response to a change in the characteristic electrical signal from one or more of the plurality of nanofiber chemical sensors, and distinguish between the first chemical and the second chemical, where the processor is in communication with at least one controller configured to control a position of one or more windows of the vehicle based on the detection of the first chemical and activate an air filtration system of the vehicle based on the detection of the second chemical.

2. The air quality system according to claim 1, wherein the one or more of the plurality of nanofiber chemical sensors is configured to detect organic compounds, and wherein the processor is configured to distinguish among the plurality of airborne materials in response to electrical characteristics detected by the plurality of nanofiber chemical sensors.

3. The air quality system according to claim 1, wherein the at least one controller is in communication with a ventilation system of the vehicle, and the at least one controller is further configured to:
   in response to the detection of one or more of the first and second chemicals, activate the ventilation system.

4. The air quality system according to claim 3, wherein the ventilation system is configured to introduce exterior air in the compartment of the vehicle and decrease a concentration of the one or more of the first and second chemicals.

5. The air quality system according to claim 4, wherein the at least one controller is further configured to:
   identify the first and second chemicals in response to the characteristic electrical signal from the one or more of the plurality of nanofiber chemical sensors exceeding a predetermined threshold; and
   control the ventilation system to introduce the exterior air while the characteristic electrical signal exceeds the predetermined threshold.

6. The air quality system according to claim 3, wherein the ventilation system includes an HVAC system.

7. The air quality system according to claim 3, wherein the ventilation system is in communication with an air supply port configured to draw exterior air into the compartment of the vehicle.

8. The air quality system according to claim 1, wherein the at least one controller is in communication with an ignition system of the vehicle, and in response to the detection of one or more of the first and second chemicals, the at least one controller is configured to control the ignition system.

9. The air quality system according to claim 1, wherein the at least one controller is in communication with an alert device, and in response to the detection of one or more of the plurality of airborne materials, the at least one controller is configured to control the alert device to output a notification of the one or more of the plurality of airborne materials.

10. The air quality system according to claim 1, wherein the at least one controller is further configured to:
    access a user profile comprising information identifying a user-defined material that corresponds to one of the first chemical and the second chemical, the user-defined material being associated with the user profile.

11. The air quality system according to claim 10, wherein the at least one controller is further configured to:
    in response to an activation of the user profile and the detection of the user-defined material exceeding a user-defined detection level, activating an alert device configured to communicate the detection of the user-defined material.

12. The air quality system according to claim 11, wherein the user-defined detection level corresponds to a non-zero concentration of the one of the first chemical and the second chemical.

13. The air quality system according to claim 12, wherein the allergen user-defined material is specific to an occupant of the vehicle or a class of users afflicted by an allergy.

14. The air quality system according to claim 1, wherein the air filtration system includes one or more of an active filter, an air purifier, a UV-C air filter, and an ionizer.

15. The air quality system according to claim 1, wherein controlling the position of the one or more windows of the vehicle includes closing the one or more windows in response to detection of the first chemical.

16. A method for controlling an air quality system for a vehicle, the method comprising:
    via a plurality of nanofiber chemical sensors, detecting a first chemical and a second chemical different than the first chemical, the first and second chemicals associated with a plurality of airborne materials in a compartment of the vehicle;
    monitoring characteristic electrical signals from the plurality of nanofiber chemical sensors;
    generating a detection signal in response to a change in one or more of the characteristic electrical signals;

distinguishing among the plurality of airborne materials based on detection of the first and second chemicals; and communicating the detection signal to at least one controller configured to control a position of one or more windows of the vehicle based on the detection of the first chemical and activate an air filtration system of the vehicle based on the detection of the second chemical.

17. The method according to claim 16, further comprising:

in response to the detection of one or more of the plurality of airborne materials, activating a ventilation system introducing exterior air in the compartment of the vehicle.

18. The method according to claim 16, further comprising:

in response to the detection of the one or more of the plurality of airborne materials, controlling an ignition system of the vehicle to control a vehicle ignition state.

19. An air quality system for a vehicle comprising:

a chemical detection apparatus comprising a plurality of nanofiber chemical sensors configured to detect a first chemical and a second chemical different than the first chemical, the first and second chemicals associated with a plurality of airborne materials in a compartment of the vehicle, wherein the plurality of nanofiber chemical sensors are each configured to adjust a characteristic electrical signal in response to changes in the presence of the plurality of airborne materials; and a processor coupled to the plurality of nanofiber chemical sensors, wherein the processor is configured to monitor the characteristic electrical signal from each of the plurality of nanofiber chemical sensors and generate a detection signal in response to a change in the characteristic electrical signal from one or more of the plurality of nanofiber chemical sensors, and the processor is in communication with at least one controller, wherein the at least one controller is configured to:

access information identifying a first user-defined material and a second user-defined material, wherein the first user-defined material corresponds to the first chemical and the second user-defined material corresponds to the second chemical;

in response to detection of the first chemical exceeding a first user-defined detection level, control a position of one or more windows of the vehicle; and in response to detection of the second chemical exceeding a second user-defined detection level, control an active air filter of the vehicle.

20. The air quality system according to claim 19, wherein the at least one controller is further configured to:

in response to detection of one of the first user-defined material and the second user-defined material exceeding one of the first and second user-defined detection levels, activate an alert device configured to communicate the detection of the one of the first user-defined material and the second user-defined material.

* * * * *